(12) United States Patent
Johnson et al.

(10) Patent No.: US 11,940,099 B2
(45) Date of Patent: Mar. 26, 2024

(54) GAS FLOW ALARM

(71) Applicant: BPR MEDICAL LIMITED, Mansfield (GB)

(72) Inventors: Benjamin Johnson, Mansfield (GB); Martin Cooper, Mansfield (GB); Michael Brudenell, Mansfield (GB); Richard Radford, Mansfield (GB)

(73) Assignee: BPR Medical Limited, Mansfield (GB)

( * ) Notice: Subject to any disclaimer, the term of this patent is extended or adjusted under 35 U.S.C. 154(b) by 280 days.

(21) Appl. No.: 17/436,994

(22) PCT Filed: Mar. 6, 2020

(86) PCT No.: PCT/GB2020/050542
§ 371 (c)(1),
(2) Date: Sep. 7, 2021

(87) PCT Pub. No.: WO2020/178600
PCT Pub. Date: Sep. 10, 2020

(65) Prior Publication Data
US 2022/0178500 A1 Jun. 9, 2022

(30) Foreign Application Priority Data
Mar. 7, 2019 (GB) .................................. 1903074

(51) Int. Cl.
*F17C 13/02* (2006.01)
*A61M 16/00* (2006.01)
(Continued)

(52) U.S. Cl.
CPC ......... *F17C 13/02* (2013.01); *A61M 16/0003* (2014.02); *A61M 16/0051* (2013.01);
(Continued)

(58) Field of Classification Search
CPC .............. F17C 13/02; F17C 2205/0329; F17C 2205/0335; F17C 2205/0338;
(Continued)

(56) References Cited

U.S. PATENT DOCUMENTS 2,436,522 A * 2/1948 Meidenbauer, Jr. ...... A62B 7/12
137/81.1
3,831,595 A * 8/1974 Valenta ............. A61M 16/0051
128/205.15
(Continued)

FOREIGN PATENT DOCUMENTS

CA 2689454 A1 * 12/2008 ........ A61M 16/0051
EP 0960629 A2 * 12/1999 .......... A61M 16/202
(Continued)

OTHER PUBLICATIONS

Application No. GB1903074.1 Search Report under Section 17 dated Sep. 4, 2019, 3 pages.

*Primary Examiner* — Chico A Foxx
(74) *Attorney, Agent, or Firm* — Keller Preece PLLC

(57) ABSTRACT

Aspects and embodiments relate to a gas flow alarm apparatus and gas flow alarm method. The apparatus comprises: a device configurable to introduce back pressure into a flow of gas, a supply sensor configured to determine whether gas flow to the device is enabled; a pressure sensor configured to determine whether a flow of gas through the device has developed back pressure; and logic circuitry in communication with the supply sensor and the pressure sensor configured to determine whether gas flow to the device is enabled and whether a flow of gas through the device has developed back pressure and, if not, to activate an alarm condition. Aspects and embodiments can provide a system which operates to warn a user against various adverse (Continued)

conditions in which a flow of therapeutic gas to a patient is required, yet not being provided.

18 Claims, 7 Drawing Sheets

(51) Int. Cl.
*A61M 16/10* (2006.01)
*A61M 16/20* (2006.01)

(52) U.S. Cl.
CPC ...... *A61M 16/1005* (2014.02); *A61M 16/208* (2013.01); *A61M 2016/0027* (2013.01); *A61M 2016/0033* (2013.01); *A61M 2205/581* (2013.01); *F17C 2205/0329* (2013.01); *F17C 2205/0335* (2013.01); *F17C 2205/0338* (2013.01); *F17C 2205/035* (2013.01); *F17C 2221/011* (2013.01); *F17C 2223/0123* (2013.01); *F17C 2250/036* (2013.01); *F17C 2250/043* (2013.01); *F17C 2250/0443* (2013.01); *F17C 2270/025* (2013.01)

(58) Field of Classification Search
CPC .......... F17C 2205/035; F17C 2221/011; F17C 2223/0123; F17C 2250/036; F17C 2250/043; F17C 2250/0443; F17C 2270/025; A61M 16/0003; A61M 16/1005; A61M 16/0051; A61M 16/208; A61M 2016/0027; A61M 2016/0033; A61M 2205/581
See application file for complete search history.

(56) References Cited

U.S. PATENT DOCUMENTS

| | | | | |
|---|---|---|---|---|
| 5,038,770 A * | 8/1991 | Perkins | .................. | A61M 16/10 128/205.24 |
| 5,603,315 A | 2/1997 | Sasso | | |
| 5,727,589 A * | 3/1998 | Yokogi | .................. | F17C 7/00 141/85 |
| 6,012,478 A * | 1/2000 | Park | .................. | F17C 13/04 137/240 |
| 6,067,022 A * | 5/2000 | Laswick | .................. | A62B 9/006 340/626 |
| 6,089,229 A * | 7/2000 | Bathe | .................. | A61M 16/12 128/204.21 |
| 6,164,276 A | 12/2000 | Bathe et al. | | |
| 6,209,579 B1 * | 4/2001 | Bowden | .................. | F17C 13/025 137/557 |
| RE38,183 E * | 7/2003 | Kosich | .................. | H05B 41/34 340/331 |
| 7,032,606 B1 * | 4/2006 | Lucas, Jr. | .................. | G05D 16/2046 137/12 |
| 2003/0189492 A1 * | 10/2003 | Harvie | .................. | A61M 16/0051 340/611 |
| 2004/0034339 A1 * | 2/2004 | Stoller | .................. | A61B 1/3132 606/1 |
| 2006/0070458 A1 * | 4/2006 | Jones | .................. | A61M 16/0672 73/861 |
| 2008/0060656 A1 * | 3/2008 | Isaza | .................. | A61M 16/0468 128/207.16 |
| 2008/0139954 A1 * | 6/2008 | Day | .................. | A61N 1/3956 600/523 |
| 2009/0205655 A1 * | 8/2009 | Montgomery | .... | A61M 16/0875 128/203.14 |
| 2011/0248856 A1 * | 10/2011 | Obenchain | .......... | A61M 16/085 340/606 |
| 2012/0180790 A1 | 7/2012 | Montgomery et al. | | |
| 2015/0000659 A1 * | 1/2015 | Martin | .............. | A61M 16/0672 128/203.22 |
| 2015/0132156 A1 * | 5/2015 | Honda | .................. | F04B 27/1063 417/269 |
| 2017/0266399 A1 * | 9/2017 | Campana | ............ | A61M 16/107 |
| 2017/0361043 A1 * | 12/2017 | Krüger | .............. | A61M 16/0051 |
| 2020/0345961 A1 * | 11/2020 | Martin | .............. | A61M 16/0066 |

FOREIGN PATENT DOCUMENTS

| | | | | |
|---|---|---|---|---|
| EP | 960630 A2 * | 12/1999 | .............. | A61F 2/06 |
| EP | 1645303 | 4/2006 | | |
| EP | 2498849 B1 * | 8/2022 | .............. | A61M 16/00 |
| GB | 2418738 A * | 4/2006 | ........ | A61M 16/0666 |
| WO | 2017/102537 | 6/2017 | | |
| WO | WO-2017102537 A1 * | 6/2017 | ............ | F17C 13/025 |

* cited by examiner

GAS FLOW ALARM

FIELD OF THE INVENTION

Aspects and embodiments relate to a gas flow alarm apparatus and gas flow alarm method. In particular, aspects and embodiments relate to a therapeutic gas flow alarm apparatus, for use in patient delivery applications.

BACKGROUND

Patients requiring therapeutic gas, for example, oxygen, may typically be administered that therapeutic gas via delivery equipment. That delivery equipment is often connected to a gas source via flexible plastics tubing and administration may occur in a domestic or clinical environment. Oxygen therapy can be a critical treatment for patients suffering from hypoxemia.

Oxygen supplied in pressurised cylinders is a common source of therapeutic gas supply in emergency or acute care applications. Pressurised oxygen cylinders typically fall into two categories: those with a valve integrated pressure regulator (VIPR) fitted and those with only a cylinder valve. VIPR types usually include a flow meter, for example, a flowmeter having a fixed orifice configuration and a rotary dial that is used to select a desired flow rate for a patient. Cylinders only having a cylinder valve require a pressure regulator or pressure regulator with a flow control function to be fitted to the gas cylinder before it can be used.

Reports have highlighted risks associated with unintentional non-delivery of oxygen therapy or premature cessation of oxygen flow in oxygen therapy. Those risks are typically associated with therapeutic gas delivery systems in which a portable oxygen supply, for example, a pressurised gas cylinder, is used in emergency or acute care applications.

It is desired to provide a means to mitigate possible non-delivery or premature cessation of oxygen in a therapeutic gas delivery system.

SUMMARY

A first aspect provides a gas flow alarm apparatus comprising: a device configurable to introduce back pressure into a flow of gas; a supply sensor configured to determine whether gas flow to the device is enabled; a pressure sensor configured to determine whether a flow of gas through the device has developed back pressure; logic circuitry in communication with the supply sensor and the pressure sensor, the circuitry being configured to determine whether gas flow to the device is enabled and whether a flow of gas through the device has developed back pressure and, if not, to activate an alarm condition.

The first aspect recognises that whichever type of pressurised cylinder is used for therapeutic gas delivery, there are a number of hazardous situations that can arise through, for example, equipment failure, contamination and/or poor usability of oxygen supply systems. A non-exhaustive list of potential hazardous situations includes the following scenarios:

1. A user takes any type of oxygen cylinder and opens the cylinder valve. The user selects an oxygen flow by setting the dial correctly but there is no flow because the cylinder is empty since the user has not checked the pressure gauge.
2. A user takes any type of oxygen cylinder and opens the cylinder valve. The user selects an oxygen flow by setting the dial correctly but there is no flow since the pressure gauge is faulty and is stuck in a position showing gas is available when, in fact, the cylinder is empty.
3. A user takes an integral valve oxygen cylinder but does not open the cylinder valve. The user selects an oxygen flow by setting the dial correctly but there is no flow since the cylinder valve is not open.
4. A user takes any type of oxygen cylinder and opens the cylinder valve. The user selects an oxygen flow but accidentally leaves the dial set between settings and there is no flow to the patient.
5. A user takes any type of oxygen cylinder and opens the cylinder valve. The user selects an oxygen flow but purposefully sets the dial between settings to achieve a flow between the two settings indicated, with the intention of delivering a flow rate between adjacent settings. There is no oxygen flow to the patient.
6. A user takes any type of oxygen cylinder and opens the cylinder valve. The user selects an oxygen flow by setting the dial correctly but there is no flow as a result of the flow control orifice selected being blocked.
7. A user takes any type of oxygen cylinder and opens the cylinder valve. The user selects and oxygen flow by setting the dial correctly and checks the cylinder contains sufficient gas but the oxygen runs out during use (for example, due to miscalculation of time remaining, an unidentified gas leakage and/or handing a patient over to a different carer part way through therapy).

Such examples relate to oxygen supplies from oxygen cylinders but some of these hazardous situations can also be present where the oxygen is supplied from an oxygen pipeline in a hospital, a liquid oxygen supply or the flow of oxygen from an oxygen concentrator.

One way to reduce the occurrence of some of these hazardous situations is to monitor content of a gas cylinder and calculate time remaining at a selected flow rate by measuring pressure decay. Examples of such arrangements are given in, for example, EP3097343 or US2016024542. Those arrangements require gas cylinder pressure to be sensed. The first aspect provides an alternative arrangement in which cylinder pressure need not be continuously monitored to provide an indication of whether a therapeutic gas flow is being delivered to a patient. That is to say, the first aspect provides a simple mechanism by which to provide a gas flow alarm to a user. The first aspect recognises that it is possible to implement a simple, inexpensive mechanism to check whether there is gas flow in a gas delivery line and whether that gas flow is intended.

The first aspect can provide a gas flow alarm apparatus. That gas flow alarm may comprise a therapeutic gas flow alarm. The alarm may comprise a pressurised gas cylinder gas flow alarm. The alarm may comprise a device configurable to introduce back pressure into a flow of gas. That is to say, a device or element may be arranged in a gas line such that when gas flows through that gas line, through the device, back pressure is introduced into that gas flow. The gas flow alarm may comprise a supply sensor. That supply sensor can be configured to sense or otherwise determine whether gas flow to the device is enabled. In other words, the supply sensor is configured to sense whether gas is free to flow from a supply through the gas line in which the device can be placed. The alarm can also include a pressure sensor configured to determine whether a flow of gas through the device has developed back pressure. The alarm can also include logic circuitry in communication with the supply sensor and the pressure sensor. The logic circuitry can be configured to receive a signal from the pressure sensor and supply sensor. The circuitry can be configured to determine, based on the received signals from the sensors, whether gas flow to the device is enabled and whether a flow of gas through the device has developed back pressure. The logic can be configured such that an alarm condition can be activated if signals from the sensors indicate that no back-pressure through the device has been developed, even though a gas flow to the device is enabled.

In some embodiments, the gas flow alarm apparatus further comprises: an alarm sounder activatable by the alarm condition. The logic circuitry may be configured to communicate with said alarm. The logic circuitry can be configured to trigger activation of the alarm sounder when the alarm condition is determined to be met. In some embodiments, an audible alarm signal is generated by the alarm sounder when the logic circuitry detects a non-zero supply flow and back pressure across the device is not sensed. Accordingly, an audible signal may be provided to a user to indicate that there may be an issue with an intended gas flow to a patient. It will be appreciated that other alarm indicators could be triggered by the alarm condition. For example, the logic circuitry may be in communication with a visual indicator, for example, a warning lamp. In some arrangements, the logic circuitry may be in communication with a device, for example, a mobile communication device, such as a mobile phone or tablet, and trigger a warning indication on that device.

In some embodiments, the audible alarm signal or other indicator to a user is generated after the logic circuitry detects the non-zero supply flow and the back pressure across the device is not sensed after a predetermined time delay. In other words, the alarm condition may only be triggered by the logic circuitry if the pressure sensor and supply sensor meet the alarm criteria for a predetermined time period. Accordingly, false detection of the alarm condition can be avoided.

In some embodiments, the audible alarm signal is a high priority oxygen alarm according to IEC 60601-1-8.

In some embodiments, the gas flow alarm apparatus further comprises: an electrical energy source configured to supply the alarm sounder with electrical energy, wherein the logic circuitry is configured to supply electrical energy to the alarm sounder only when the alarm condition is met. Accordingly, the gas flow alarm may be energy efficient and use minimal energy when not detecting an alarm condition. Such an arrangement helps to ensure longevity of the gas flow alarm.

In some embodiments, the device comprises: a gas flow restricting orifice. In some embodiments, the device comprises: a spring valve. In some embodiments, back pressure is generated by a check valve biased to a closed position by a spring.

Accordingly, an appropriate device may be chosen to introduce back pressure into a gas flow, based on the likely flow rate, or range of flow rates, of that gas flow. The back pressure developed by the device across the range of gas flow rates for which the alarm is intended may determine the physical parameters of some components of the device. For example, dimensions of an orifice, spring dimensions and strength in the case of a spring valve. In some embodiments, the back pressure generated by the device is selected such that the back pressure is lower than 50 kPa, or 25 kPa. Such a value ensures that delivery of gas at an appropriate flow rate to a patient is not compromised by the presence of the gas flow alarm components in the gas flow.

In some embodiments, the device is locatable downstream of a supply control mechanism. In some embodiments, the device is locatable upstream of a gas flow outlet. Accordingly, the device to introduce back pressure is placed in a gas flow after a primary on/off valve at a source, that on/off relating to supply of therapeutic gas to, for example, a patient.

In some embodiments, the pressure sensor comprises a pressure switch. In some embodiments, the pressure sensor comprises a pressure transducer. It will be appreciated that any appropriate mechanism or sensor which determines whether back pressure has been developed across the device can be used.

In some embodiments, the gas flow alarm apparatus further comprises: a bleed orifice, in fluid communication with a flow outlet, configured to allow free passage of gas through the bleed orifice at a flow rate less than a lowest flow rate provided for a supply control which enables gas flow to the device. In some embodiments, the bleed orifice is arranged in parallel to the device such that a minor internal leak does not initiate the logic circuitry to initiate the alarm condition and residual pressure within the device can be discharged. Without a bleed orifice, a minor leak could prevent an alarm being initiated but would not initiate an alarm.

In some embodiments, the gas flow alarm apparatus further comprises: a supply pressure sensor configured to determine whether supply pressure has crossed a threshold; said logic circuitry being in communication with the supply sensor, the pressure sensor, and the supply pressure sensor, the circuitry being configured to determine whether gas flow to the device is enabled and whether supply pressure has crossed the threshold and, if so, to activate an alarm condition. In some embodiments the threshold comprises a low pressure threshold. The low pressure threshold may be indicative of a supply cylinder depletion. The low pressure threshold may comprise an indication that a supply cylinder requires replacement, or may be selected to indicate that cylinder replacement may be required imminently. The alarm condition may comprise an audible or visual alarm and may differ from, or be identical to, the alarm condition activated in the event of activation of an alarm condition triggered by the circuitry determining that gas flow to the device is enabled and no back pressure has been developed.

A second aspect provides a gas flow alarm method comprising: configuring a device to introduce back pressure into a flow of gas; providing a supply sensor configured to determine whether gas flow to the device is enabled; providing a pressure sensor configured to determine whether a flow of gas through the device has developed back pressure; determining from signals received from the supply sensor and the pressure sensor whether gas flow to the device is enabled and whether a flow of gas through the device has developed back pressure and, if not, activating an alarm condition.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which.

DESCRIPTION OF THE EMBODIMENTS

Figure 1:
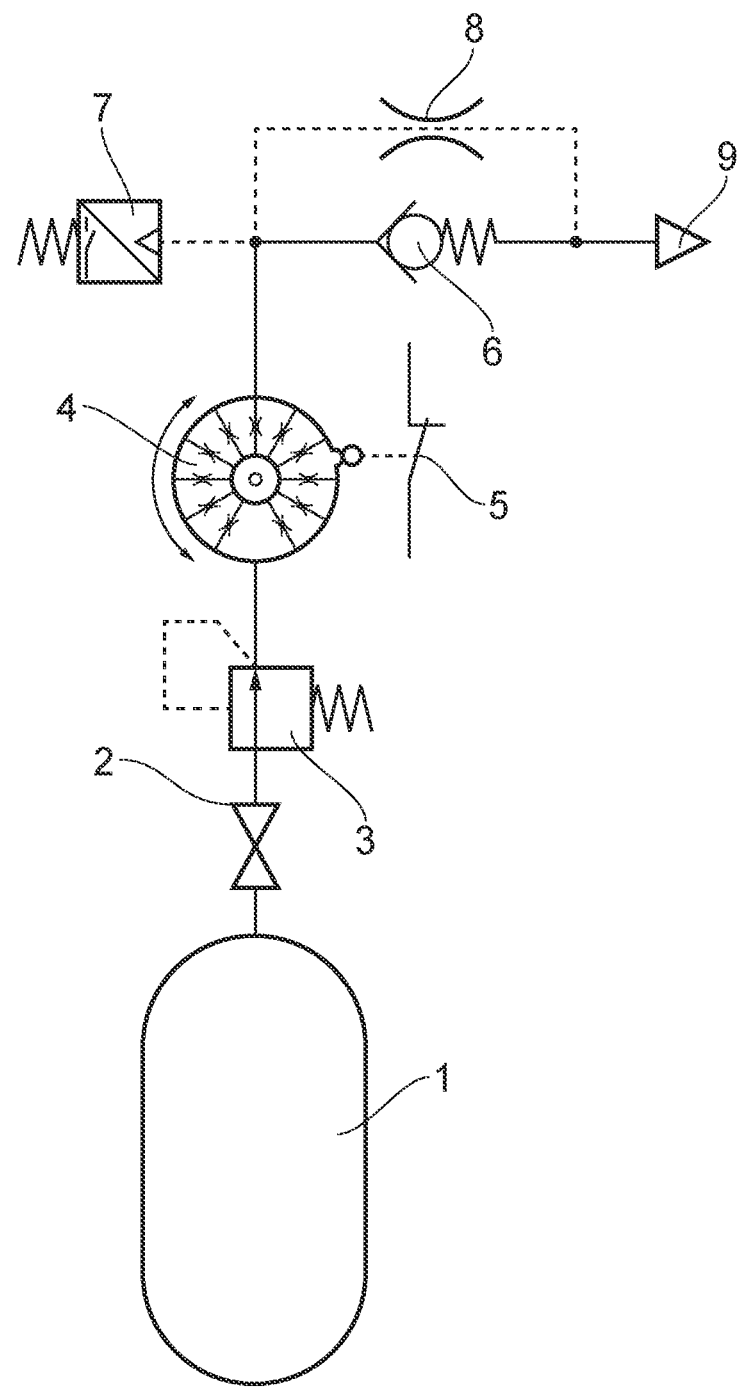
FIG. 1 illustrates schematically an arrangement according to one example.

Before describing examples in detail, a general overview is provided. Examples recognise that it is possible to provide apparatus which activates an alarm in response to a signal received from, for example, two sensor inputs. The apparatus can be placed in the gas flow line of a gas delivery system. The apparatus can include a device configurable to introduce back pressure into a gas flow. The device can include an element arranged as a gas flow restriction, for example, fixed restriction such as a fixed diameter orifice, or a sprung check valve or other variable restriction, the fixed or variable restriction being configured to introduce back pressure into the gas flow line. The apparatus can include sensors which are provided to: (i) sense back pressure associated with gas flowing through the element arranged as a gas flow restriction, thus indicating a flow of gas through the restriction element; and (ii) sense that a flow control dial is in an on position in which flow from a cylinder is enabled. In this way, it is possible to implement a simple, inexpensive mechanism to check whether there is gas flow in a gas delivery line and whether that gas flow is intended.

One example of such apparatus comprises a device including a housing connectable to a gas flow line, through which the gas intended for delivery to a patient flows. The apparatus further comprises at least two sensors and an alarm circuit with two switch inputs, one switch input associated with the sensing of back pressure through the housing and one switch input associated with the sensing of a gas flow control dial being moved from an off position to any other position. The alarm circuit can be configured such that an alarm state is energised when signals from the sensors indicate that the flow control dial is in any position other than off and no back pressure, or back pressure below a predetermined known threshold, is sensed. The apparatus may further comprise an audible sounder and the alarm state being energised may trigger the audible sounder to provide an audible warning to a user when, for example, oxygen therapy is not being provided as intended.

It will be appreciated that apparatus which operates as described above can warn a user against various adverse conditions in which a flow of therapeutic gas to a patient is required, yet not being provided. In other words, the apparatus may operate as a gas flow alarm.

Examples recognise that a device can be provided in a gas flow delivery line to deliberately introduce a resistance to gas flow. Whilst it will be appreciated that all devices in a gas delivery line introduce resistance to gas flow, a device in accordance with examples ensures the resistance introduced is at a level which can be sensed by the sensors across a range of gas flow rates, and yet not introduce resistance at a level which interrupts or disturbs an intended flow of gas to a patient. That resistance introduces back pressure between gas flow into the device and out of the device. Aspects recognise that the resistance to gas flow can be utilised as mechanism to sense gas flow through a device, or along a gas delivery line.

It is common for fixed orifice type flowmeters to be provided with portable oxygen cylinders for healthcare purposes. Such flowmeters typically do not have any indication of gas flow other than a number engraved or printed on a selection dial which indicates a flow to be provided if that number is aligned with a viewing window or some other visible alignment indicator. In this circumstance, if apparatus according to arrangements described introduced too great a back pressure, a user providing oxygen therapy to a patient could have no awareness that a back pressure, (higher than that for which the flow control orifice is back pressure compensated) is present in the flow line and that the indicated flow may not be within the limits of accuracy stated within the specification of the flow control device. A situation such as this could result in the delivery of suboptimal care.

Figure 5:
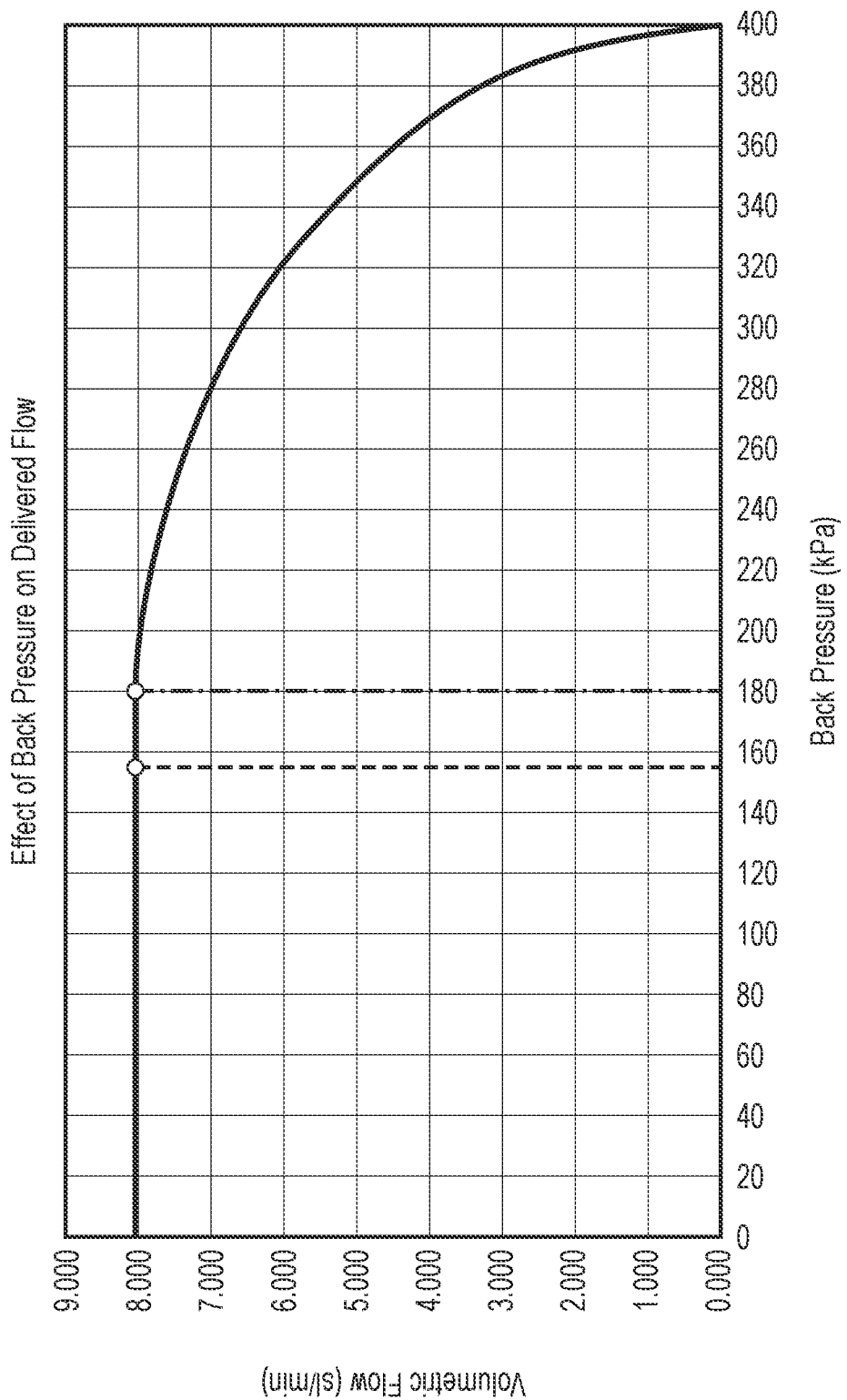
FIG. 5 illustrates the effect of increasing back pressure on volumetric flow delivered.

FIG. 5 illustrates the effect of increasing back pressure on volumetric flow delivered.

Oxygen flowmeters fitted to most portable oxygen supply types operate with a significant differential pressure across the flow control orifices. The ratio of downstream to upstream pressure is maintained at a level significantly below a critical level at which the flow would become unchoked, thereby ensuring that the system operates to maintain a mass flow with significant downstream pressure. By way of example, if oxygen pressure upstream of a flow control orifice is 501.3 kPa absolute pressure, mass flow remains constant up to a downstream absolute pressure of 265.0 kPa, where downstream pressure is given by:

$$P_{critical} = P_{upstream} * (2/(\gamma+1))^{(\gamma/(\gamma-1))}$$

Where: γ is the ratio of specific heats (i.e. Cp/Cv), which for oxygen at 15° C. is 1.3977

Any back pressure introduced by gas flow alarm components must therefore be small enough so as not to reduce the available pressure to downstream devices to a level that would cause the pressure across the flowmeter flow control orifice to become subcritical and therefore unchoked.

FIG. 1 illustrates schematically an arrangement according to one example. The arrangement shown generally in FIG. 1 comprises a gas supply 1 in the form of a pressurised gas cylinder. The arrangement further comprises a gas cylinder valve 2, which is configured to provide a binary on/off in relation to the gas supply 1, a pressure regulator 3 and a flowmeter 4. The flowmeter 4 is configured to modulate the flow rate of gas from the supply 1. Flowmeter 4 shown in FIG. 1 comprises a dial type orifice flowmeter having 11 flow rates and an "off" position. In the "off" position, no gas may flow from the supply to a patient. When in one of the other positions, gas is able to flow along a gas delivery line to a patient, or patient delivery apparatus, for example, located at gas outlet 9.

Apparatus is shown in FIG. 1 which can allow a check to be made regarding delivery of gas to a patient or patient delivery apparatus located at gas outlet 9. Such apparatus comprises a "push to make" electrical microswitch 5, which is configured to detect whether the flowmeter 4 is in the off position, or in one of the 11 "on" positions. In the arrangement shown in FIG. 1, the apparatus further comprises a spring assisted one-way valve 6 which is used to introduce back pressure into the flow of gas from supply 1 to outlet 9. The apparatus also includes a pressure switch 7 which is arranged to be normally closed but break contact with rising pressure. The arrangement of FIG. 1 also comprises a bleed orifice, the purposes of which are described further below.

The apparatus is configured such that the one-way valve 6 only develops a small back pressure before it opens. This is because some respiratory medical devices that are, for example, connected to medicinal air or medicinal oxygen gas cylinders, introduce a significant back pressure and their function is dependent upon that back pressure being present. Introducing a further large back pressure would introduce significant error in the gas flow rate metered by an upstream flow control device. For example, a jet nebuliser, which is used to aerosolise liquid pharmaceutical mixture for inhalation is typically driven by medicinal air and medicinal oxygen with a standard volumetric flow rate of 6 or 8 litres per minute. Such a device may incorporate a small orifice such a 0.65 mm diameter, which introduces a back pressure of approximately 155 kPa downstream of an upstream critical flow control orifice at a standard oxygen flow rate of 8 litres per minute. It is therefore important that the apparatus provided as a means of sensing flow (due to a back pressure developed downstream of a flow control orifice) does not introduce excessive back pressure, such as more than 25 kPa, so that the accuracy of the upstream flowmeter is not adversely affected.

Apparatus such as that shown schematically in FIG. 1 can be configured to operate as a gas flow alarm. The apparatus incorporates a means of developing back pressure. In the example shown, that means comprises a spring-assisted one-way valve, 6. Such a mechanism is particularly suited to instances in which gas flow from a supply can range from 0.5 to 25 litres a minute, without resulting in a very wide range of back pressures being developed across the full range of different flow rates. It will be appreciated that the strength/resistance of the spring can be selected such that the range of back pressures developed across the range of gas flows can be detected appropriately and do not impact upon the operation of gas delivery to a patient. In an application in which a smaller range of flow rates may need to be accommodated, it may be possible, for example, for the mechanism to develop back pressure to comprise a flow orifice or similar. It will be appreciated that the means to generate back pressure is placed such that it is located in a gas flow path downstream of a critical flow control orifice (the flowmeter 4) and upstream of a flow outlet (gas outlet 9).

The gas flow alarm apparatus shown in FIG. 1 comprises a means of sensing back pressure developed when gas is flowing through the apparatus. The means of sensing back pressure in the arrangement of FIG. 1 comprises pressure switch 7. The apparatus also comprises a means of sensing when a gas flow has been selected by a user, in the form of electrical microswitch 5.

The components of the gas flow alarm apparatus are configured to trigger an alarm state when a user selects a non-zero flow position; that is to say, the microswitch determines that the flow is not intended to be zero, and a back pressure is not sensed by pressure switch 7. The apparatus may further comprise a sounder and when the alarm state is triggered, an audible alarm signal can be generated. The audible alarm signal can be generated when a user selects a non-zero flow position and no back pressure is sensed after a short and predetermined time delay. The audible alarm signal may comprise a high priority oxygen alarm according to IEC 60601-1-8. In order to ensure alarm apparatus longevity, an electrical energy source may be provided and configured such that it only supplies electrical energy to the alarm circuit when the apparatus has triggered an alarm state. In the interest of energy saving and thus the longevity of any power source required in relation to the flow alarm apparatus, various other implementations and arrangements of components can be accommodated. For example, in relation to a sensor used to detect back pressure, if a pressure input to the system is derived from an output of a pressure transducer, output polling could be employed to minimise energy consumption by that method.

In the example of FIG. 1, back pressure is generated by a check valve biased to a closed position by a spring. The spring assisted one-way valve located downstream of a flow control orifice is configured to open at a pressure significantly lower than a critical pressure associated with a requirement to maintain choked flow across the flow control orifice. In some examples, that opening pressure is around 25 kPa.

In the example of FIG. 1, the back pressure generated when gas flows through the apparatus is sensed by a pressure switch. In alternative examples, the back pressure can be sensed by a pressure transducer. In the example shown in FIG. 1, the back pressure sensing means is located downstream of an orifice selection means which is user adjustable between at least two discrete flow rates, that is to say, the flowmeter, 4.

In the example of FIG. 1, the microswitch 5 is configured to detect when a flow selection has been made by a flow control dial being rotated from an off position.

The example of FIG. 1 includes a bleed orifice 8, in fluid communication with the flow outlet 9, configured to allow free passage of gas at a flow rate less than the lowest flow rate provided for by the selectable means of flow control. The bleed orifice is located in parallel to the spring assisted check valve, such that any minor internal leak would not prevent an alarm condition being initiated, for example, if a flow control dial was between settings after previously providing a gas flow. The bleed valve also allows residual pressure can be discharged, thereby closing the pressure switch when the flowmeter is set to an off position after supplying a gas flow.

Figure 2:
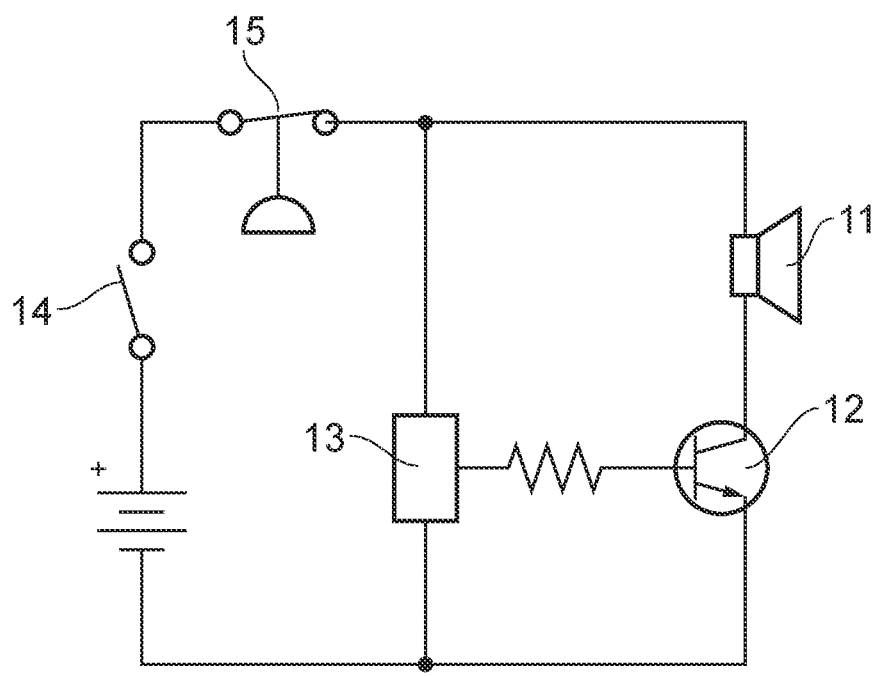
FIG. 2 illustrates schematically a basic circuit diagram associated with gas flow alarm apparatus such as that included within an arrangement shown in FIG. 1.

FIG. 2 illustrates schematically a basic circuit diagram associated with gas flow alarm apparatus such as that included within an arrangement shown in FIG. 1. A microcontroller 13 is provided to communicate with normally open microswitch 14 (when a gas supply, for example, flowmeter controlling flow from a pressured gas cylinder, is turned on, the switch closes); normally closed pressure switch 15 (when backpressure is developed, the pressure switch opens); and transistor 12. The microcontroller 13 is configured to control operation of loudspeaker 11 in dependence upon signals received from the microswitch 14 and pressure switch 15. The circuit shown operates to control an alarm circuit based upon two switch inputs, one switch input associated with the sensing of back pressure in a gas flow and one switch input associated with the sensing of a gas flow control dial being moved from an off position to any other position. The alarm circuit is configured such that an alarm state, in which the loudspeaker 11 sounds, is energised when signals from the sensors 14 and 15 indicate that the flow control dial is in any position other than off and no back pressure, or back pressure below a predetermined known threshold, is sensed. In this way the circuit of FIG. 2 allows components of a gas flow alarm device such as that included in FIG. 1 to provide an audible warning to a user when, for example, oxygen therapy is not being provided as intended.

Figure 3:
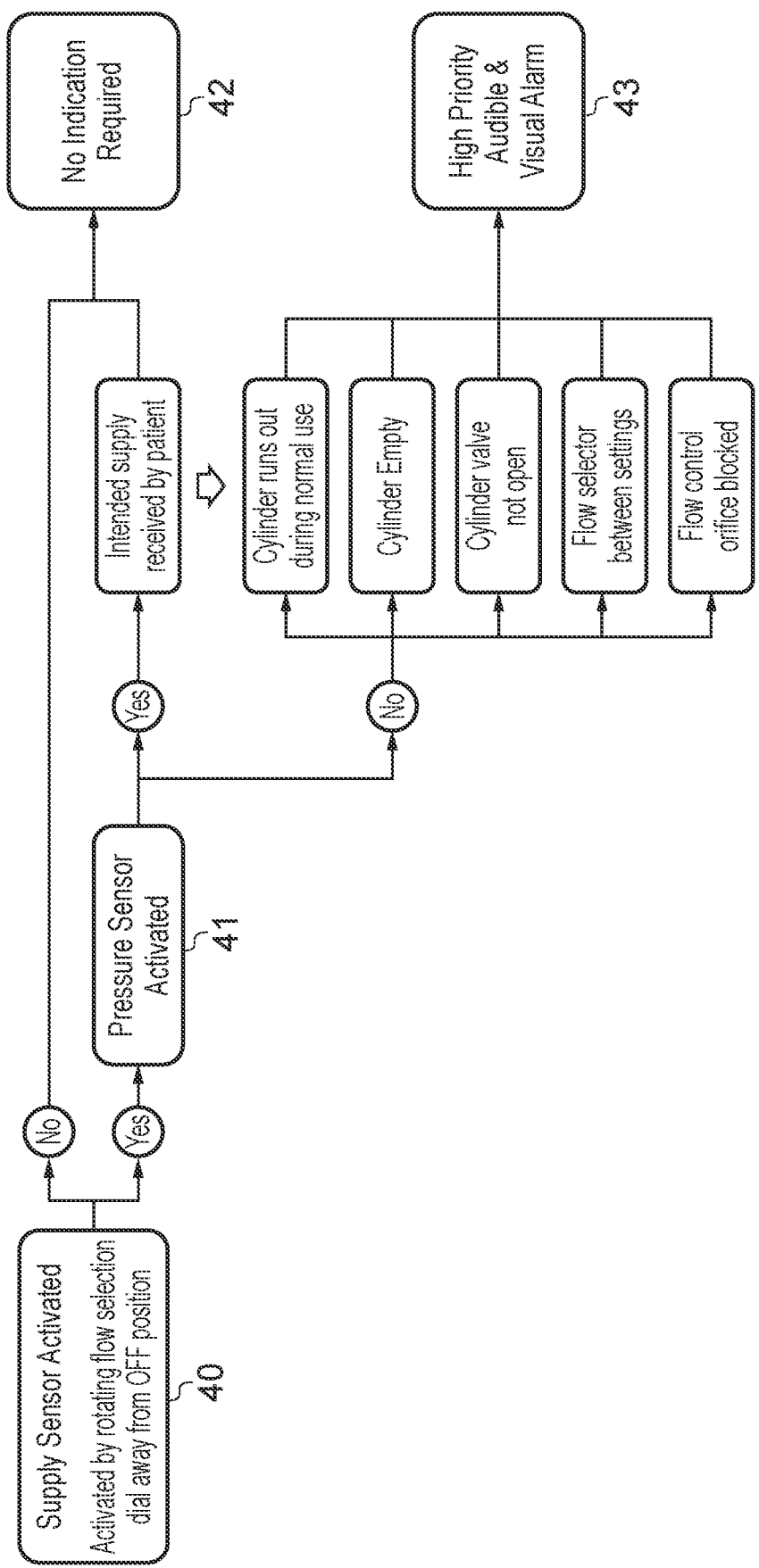
FIG. 3 is a flow diagram illustrating schematically logic processes which may be implemented by logic circuitry for use within an arrangement shown in FIG. 1.

FIG. 3 is a flow diagram illustrating schematically logic processes which may be implemented by logic circuitry for use within an arrangement shown in FIG. 1. As described above, logic circuitry is provided in communication with the supply sensor and the pressure sensor. A signal 40 can be received by the logic circuitry from the supply sensor. A signal 41 can be received by the logic circuitry from the pressure sensor. The logic circuitry is configured to activate an alarm condition 43 (or no alarm condition 42) in dependence upon the signals 41 and 42. If the supply sensor indicates that the gas supply is turned off, then no alarm condition is activated, irrespective of signal 41 from the pressure sensor. If the supply sensor indicates the supply is turned on, and the pressure sensor indicates that back pressure across the device is present, then no alarm condition is activated. If the supply sensor indicates the supply is turned on, and the pressure sensor indicates that no back pressure across the device is present, then alarm condition 43 is activated. The pressure sensor may indicate no back pressure for various reasons including, for example: a gas cylinder may have run out during normal use, the cylinder may be empty, a cylinder valve may not be open, a flow selector may be between settings (resulting in no gas flow), or a flow control orifice may be blocked.

Figure 4:
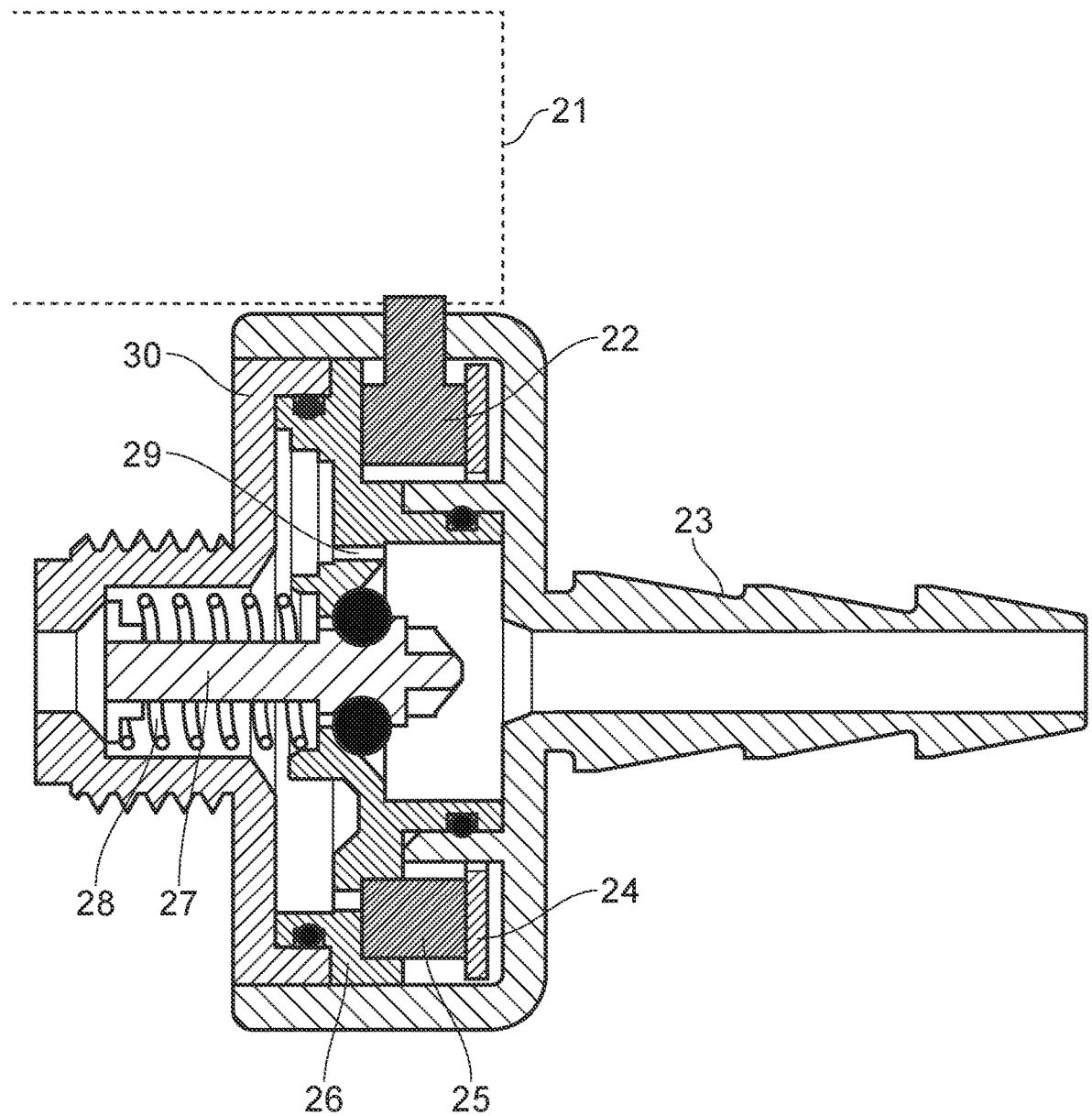
FIG. 4 is a cross sectional schematic view of main components of a device for introducing back pressure in an arrangement as shown in FIG. 1.

FIG. 4 is a cross sectional schematic view of main components of a device for introducing back pressure to in an arrangement as shown in FIG. 1. FIG. 4 illustrates main components of a gas flow alarm according to one arrangement. FIG. 4 includes an indication of a gas cylinder flow selector 21 by which a user can set a gas flow to a patient. The gas flow alarm illustrated includes a supply sensor 22 which senses whether the gas cylinder flow selector 21 is set to off, or whether a flow has been selected. A device for introducing back pressure is included in the alarm. In FIG. 4, the device is housed within a front body 23 and rear body 30 which together form a housing, that housing being locatable in a gas flow path. The device for introducing back pressure comprises inner body 26, a check valve body 27, and a spring 28. The check valve and spring arrangement introduces backpressure into a gas flow through the housing. That back pressure can be detected by pressure sensor 25. Logic circuitry is provided on a Printed Circuit Board 24. The logic circuitry is in communication with sensors 22 and 25 and is configured to operate in accordance with the flow diagram of FIG. 3. The alarm apparatus shown in FIG. 4 also includes a bleed orifice 29 which can mitigate chances of the alarm detecting false alarm conditions.

Whilst arrangements have been described in which the gas flow alarm is provided downstream of a supply control orifice, it is possible to implement alarm apparatus configured to sense regulated pressure upstream of a critical (supply control) orifice instead of downstream. It will be appreciated that when monitoring the presence of pressure upstream of the critical orifice, setting between flow positions or occlusion of an orifice cannot be identified.

Figure 6:
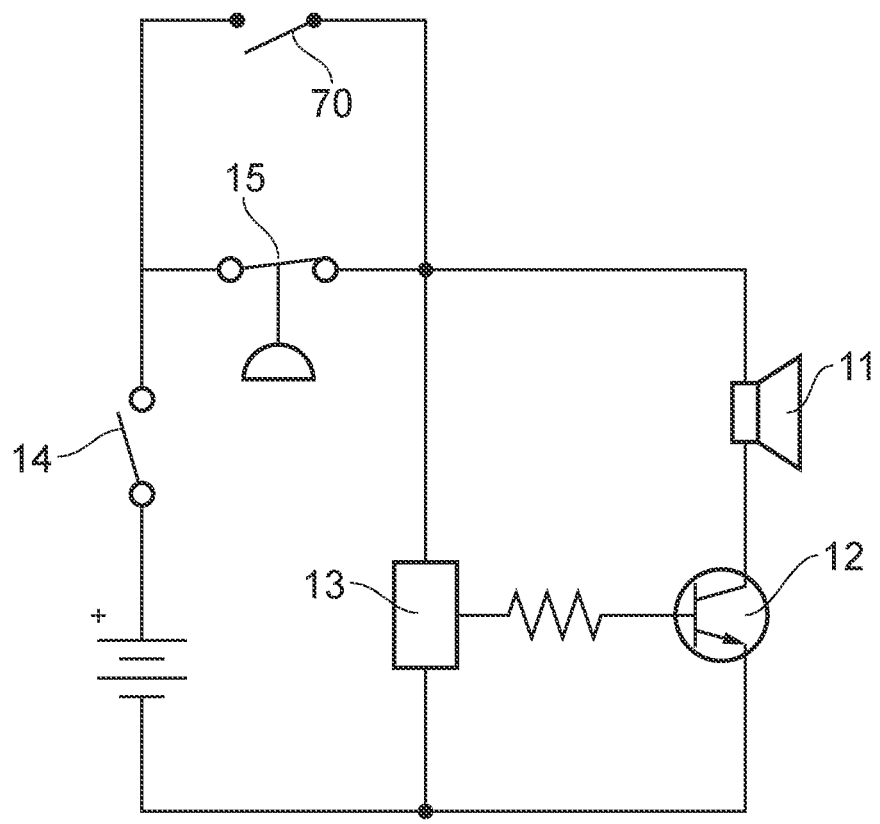
FIG. 6 illustrates schematically an alternative basic circuit diagram associated with gas flow alarm apparatus such as that included within an arrangement shown in FIG. 1.

FIG. 6 illustrates schematically an alternative basic circuit diagram associated with gas flow alarm apparatus such as that included within an arrangement shown in FIG. 1. FIG. 6 represents a development of the arrangement shown in FIG. 2 and, as such, like parts are labelled with the same reference numerals. The arrangement of FIG. 6 includes a cylinder pressure alarm function. That function is supported by providing a pressure activated microswitch 70. As before, a simplified circuit diagram associated with gas flow alarm apparatus is shown. A microcontroller 13 is provided to communicate with: normally open microswitch 14 (when a gas supply, for example, flowmeter controlling flow from a pressured gas cylinder, is turned on, the switch closes); normally closed pressure switch 15 (when backpressure is developed, the pressure switch opens); and normally open microswitch 70 (when pressure in a cylinder drops below a selected value, for example, less than 35 bar, the switch closes); and transistor 12. The microswitch 70 associated with cylinder pressure is provided in series with gas supply microswitch 14 and in parallel with backpressure microswitch 15. The microcontroller 13 is configured to control operation of loudspeaker 11 in dependence upon signals received from the microswitch 14, pressure switch 15 and cylinder pressure microswitch 70. The circuit shown operates to control an alarm circuit based upon three switch inputs, one switch input associated with the sensing of back pressure in a gas flow, one input associated with the sensing of low pressure in the cylinder and one switch input associated with the sensing of a gas flow control dial being moved from an off position to any other position. The alarm circuit is configured such that an alarm state, in which the loudspeaker 11 sounds, is energised when signals from the sensors 14, 15 and 70 indicate that the flow control dial is in any position other than off and either: no back pressure, or back pressure below a predetermined known threshold, is sensed and/or a low pressure threshold in the supply cylinder is determined to have been passed. In this way, the circuit of FIG. 6 allows components of a gas flow alarm device such as that included in FIG. 1 to provide an audible warning to a user when, for example, oxygen therapy is not being provided as intended, or when supply of a patient is occurring but the cylinder is nearing depletion and is likely to require replacement.

Figure 7:
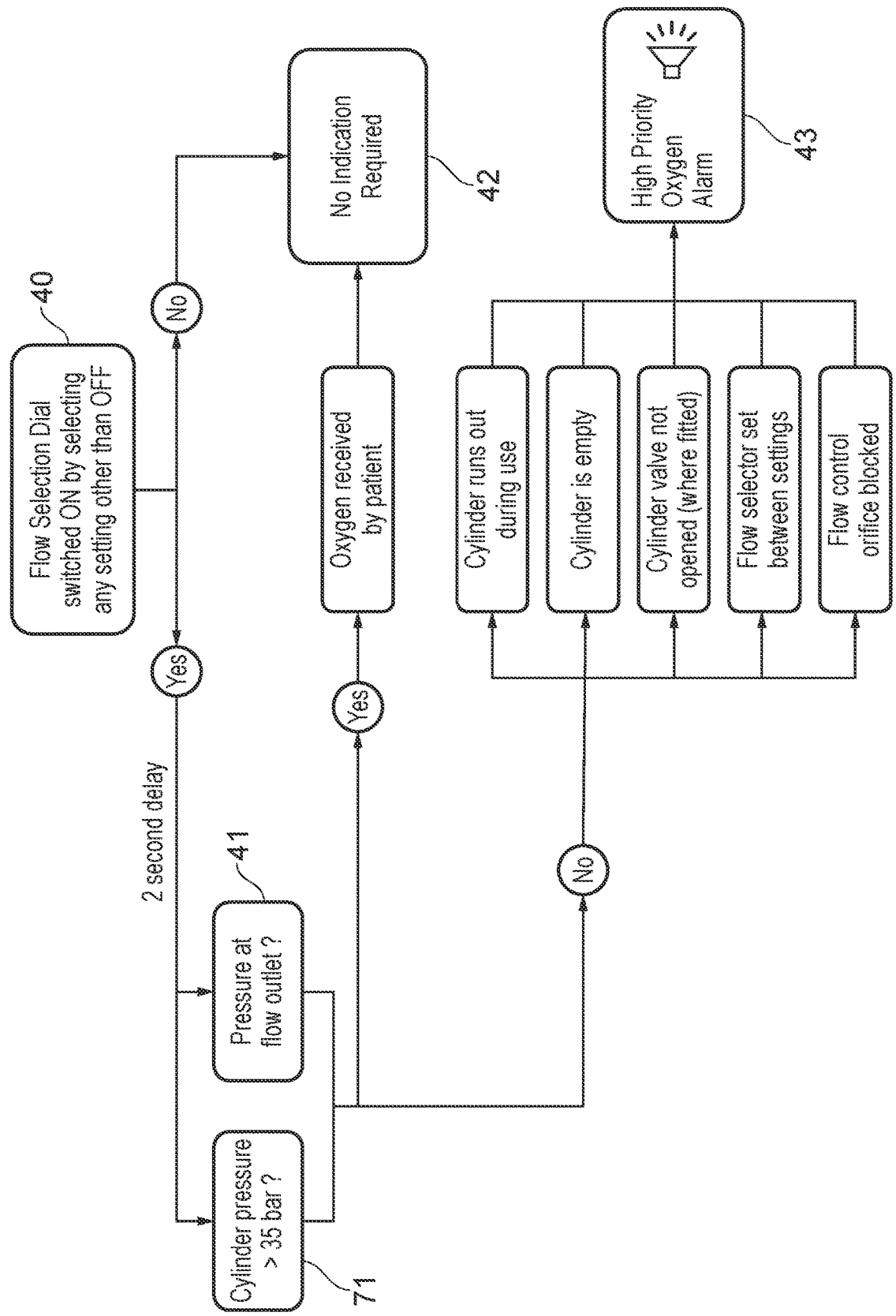
FIG. 7 is a flow diagram illustrating schematically alternative logic processes which may be implemented by logic circuitry for use within an arrangement shown in FIG. 1.

FIG. 7 is a flow diagram illustrating schematically alternative logic processes which may be implemented by logic circuitry for use within an arrangement shown in FIG. 1. As described above in relation to FIG. 6, logic circuitry is provided in communication with the supply sensor, back pressure sensor and cylinder pressure. A signal 40 can be received by the logic circuitry from the supply sensor. A signal 41 can be received by the logic circuitry from the pressure sensor. A signal 71 can be received by the logic circuitry from the cylinder pressure sensor. The logic circuitry is configured to activate an alarm condition 43 (or no alarm condition 42) in dependence upon the signals 41, 42 and 71. If the supply sensor indicates that the gas supply is turned off, then no alarm condition is activated, irrespective of signals 41 from the back pressure sensor and 71 from the cylinder pressure sensor. If the supply sensor indicates the supply is turned on, and the pressure sensor indicates that back pressure across the device is present, then no supply alarm condition is activated. If the supply sensor indicates the supply is turned on, and the cylinder pressure sensor indicates that cylinder pressure is above a selected depletion threshold, then no supply alarm condition is activated. If the supply sensor indicates the supply is turned on, and the pressure sensor indicates that no back pressure across the device is present, then alarm condition 43 is activated. The pressure sensor may indicate no back pressure for various reasons including, for example: a gas cylinder may have run out during normal use, the cylinder may be empty, a cylinder valve may not be open, a flow selector may be between settings (resulting in no gas flow), or a flow control orifice may be blocked.

Similarly, if the supply sensor indicates the supply is turned on, and the cylinder pressure sensor indicates that the cylinder pressure is below the depletion threshold, then an alarm condition 43 is activated. It will be appreciated that it is possible for alarm conditions associated with the cylinder depletion and "no delivery to patient" to be triggered simultaneously. In some arrangements the logic circuitry is configured to convey to a user the nature of the alarm condition being which has been triggered. The alarm condition associated with cylinder depletion may differ from the alarm condition associated with a "no delivery to patient" condition, since the ameliorative action associated with the latter may be more time critical.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

The invention claimed is:

1. A gas flow alarm apparatus comprising:
   a device configurable to introduce back pressure into a flow of gas;
   a supply sensor configured to determine whether supply flow to the device is enabled;
   a pressure sensor configured to determine whether the flow of gas through the device has developed back pressure;
   a bleed orifice, in fluid communication with a flow outlet, configured to allow free passage of gas through the bleed orifice at a flow rate less than a lowest flow rate provided for a supply control which enables gas flow to the device; and
   logic circuitry in communication with the supply sensor and the pressure sensor configured to:
   determine whether the supply flow to the device is enabled and whether the flow of gas through the device has developed back pressure; and
   if the supply flow is not enabled or the flow of gas has not developed back pressure, to activate an alarm condition.

2. The gas flow alarm apparatus according to claim 1, further comprising an alarm sounder activatable by the alarm condition.

3. The gas flow alarm apparatus according to claim 2, wherein an audible alarm signal is generated by the alarm sounder when the logic circuitry detects a non-zero supply flow and back pressure across the device is not sensed.

4. The gas flow alarm apparatus according to claim 3, wherein the audible alarm signal is generated after the logic circuitry detects the non-zero supply flow and the back pressure across the device is not sensed after a predetermined time delay.

5. The gas flow alarm apparatus according to claim 3, wherein the audible alarm signal is a high priority oxygen alarm according to IEC 60601-1-8.

6. The gas flow alarm apparatus according to claim 2 further comprising: an electrical energy source configured to supply the alarm sounder with electrical energy, wherein the logic circuitry is configured to supply electrical energy to the alarm sounder only when the alarm condition is met.

7. The gas flow alarm apparatus according to claim 1, wherein the device comprises a gas flow restricting orifice.

8. The gas flow alarm apparatus according to claim 1, wherein the device comprises a spring valve.

9. The gas flow alarm apparatus according to claim 1, wherein back pressure is generated by a check valve biased to a closed position by a spring.

10. The gas flow alarm apparatus according to claim 1, wherein the device is locatable downstream of a supply control mechanism.

11. The gas flow alarm apparatus according to claim 1, wherein the device is locatable upstream of a gas flow outlet.

12. The gas flow alarm apparatus according to claim 1, wherein back pressure generated by the device is selected such that the back pressure is lower than 50 kPa.

13. The gas flow alarm apparatus according to claim 1, wherein the pressure sensor comprises a pressure switch.

14. The gas flow alarm apparatus according to claim 1, wherein the pressure sensor comprises a pressure transducer.

15. The gas flow alarm apparatus according to claim 1, wherein the bleed orifice is arranged in parallel to the device such that a minor internal leak does not initiate the logic circuitry to initiate the alarm condition and residual pressure within the device can be discharged.

16. The gas flow alarm apparatus according to claim 1, further comprising: a supply pressure sensor configured to determine whether supply pressure has crossed a threshold; the logic circuitry being in communication with the supply sensor, the pressure sensor, and the supply pressure sensor, the circuitry being configured to determine whether the supply flow to the device is enabled and whether the supply pressure has crossed the threshold and, if so, to activate another alarm condition.

17. A gas flow alarm method comprising:
    configuring a device to introduce back pressure into a flow of gas;
    providing a supply sensor configured to determine whether supply flow to the device is enabled;
    providing a pressure sensor configured to determine whether the flow of gas through the device has developed back pressure;
    providing a bleed orifice, in fluid communication with a flow outlet, configured to allow free passage of gas through the bleed orifice at a flow rate less than a lowest flow rate provided for a supply control which enables gas flow to the device;
    determining from signals received from the supply sensor and the pressure sensor whether the supply flow to the device is enabled and whether the flow of gas through the device has developed back pressure; and
    if the supply flow to the device is not enabled or the flow of gas through the device has not developed back pressure, activating an alarm condition.

18. The gas flow alarm method according to claim 17, wherein providing the bleed orifice comprises arranging the bleed orifice in parallel to the device such that a minor internal leak does not initiate the alarm condition and such that residual pressure within the device can be discharged.

* * * * *